United States Patent [19]

Regnier et al.

[11] 4,132,787
[45] Jan. 2, 1979

[54] PHARMACEUTICAL COMPOSITIONS CONTAINING A GAMMA-RESORCYLIC ACID DERIVATIVE IN THE TREATMENT OF THROMBOSIS

[75] Inventors: Gilbert Regnier, Chatenay Malabry; Roger Canevari, Villebon,Yvette; Pierre Desnoyers, Fontenay aux Roses, all of France

[73] Assignee: Science Union et Cie, France

[21] Appl. No.: 688,533

[22] Filed: May 21, 1976

[30] Foreign Application Priority Data

May 30, 1975 [GB] United Kingdom ............... 23674/75

[51] Int. Cl.² ........................................... A61K 31/60
[52] U.S. Cl. .................................................. 424/230
[58] Field of Search ............................. 424/230, 317; 260/521 B

[56] References Cited

U.S. PATENT DOCUMENTS 2,385,365  9/1945  Link ................................... 424/230

OTHER PUBLICATIONS

Von Kaulla, Biochem. Pharm. vol. 16, 1967, pp. 1023–1034.
Asahina, Berichte der Deutsch Chem. Ges, Jg. 65, 1932, pp. 475–482.
Von Kaulla, Chem. Abs. vol. 67, 1967, Ab. N. 31139g.

*Primary Examiner*—Anna P. Fagelson
*Attorney, Agent, or Firm*—Gordon W. Hueschen

[57] ABSTRACT

Pharmaceutical compositions containing as active principle a γ-resorcylic acid derivative of the formula:

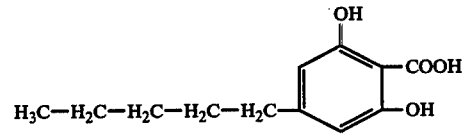

or a physiologically tolerable salt thereof.

These pharmaceutical compositions are used especially in the treatment of thromboembolic diseases and arteriosclerosis.

7 Claims, No Drawings

PHARMACEUTICAL COMPOSITIONS CONTAINING A GAMMA-RESORCYLIC ACID DERIVATIVE IN THE TREATMENT OF THROMBOSIS

The present invention provides the pharmaceutical compositions containing as active ingredient a γ-resorcylic acid derivative of the formula I:

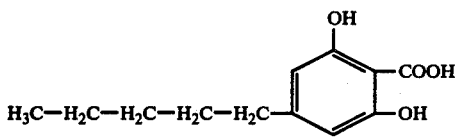

or a physiologically tolerable salt thereof, in admixture or conjunction with a pharmaceutically suitable carrier.

4-n-pentyl-6-hydroxy salicylic acid of the formula I is known especially from Berichte Der Deutsch Chem. Ges. 65 (1932) pages 475–482. It was prepared according to a known per se method which comprises submitting a mixture of 5-n-pentyl resorcinol and dried potassium carbonate to a pressure of carbon dioxide of from 50 to 100 atmospheres at a temperature of about 175° C., for one to three hours.

4-n-pentyl-6-hydroxy salicylic acid may be transformed into addition salts, especially phsyiologically tollerable salts with suitable bases such for example as alkali metal hydroxides such as sodium, potassium and lithium hydroxides, and bases, such as hydrazine, ethanolamine and ethylenediamine.

The compound of the formula I and physiologically tolerable salts thereof possess valuable pharmacological and therapeutic properties, especially thrombolytic, fibrinolytic and platelet-stickiness and -aggregation decreasing properties.

The toxicity of the compound of the formula I is low and the $LD_{50}$ in mice is within the range of 50 to 100 mg/kg I.V. and within the range of 1000 to 1500 mg/kg P.O.

The thromobolytic activity was studied in vitro by the method of Von Kaulla on the standard blood clot, Thromb. Diath. Haem. 5, 489 (1961). It was observed that the product I provokes the lysis of the clot at 0.004 to 0.0016 molar concentrations, corresponding to concentrations between 0.89 and 0.35 mg/ml.

The fibrinolytic activity was determined on a batch of 7 male rats after administration of 25 mg/kg P.O. of compound I. It was observed that the fibrinolytic activity increases respectively of 14 and 11%, 60 and 90 minutes after the administration of the product. The return to basis values takes place 3 hours after this administration.

The same activity was also demonstrated by the decrease of the level of monomers of fibrin after administration in the rabbit of 5 mg/kg I.V. of compound I. Two minutes after the injection of the product, it was observed a decrease of 10% of the lever of monomers of fibrin. This decrease reaches 23%, ten minutes after the injection.

By using the Salzman method, J. Lab. Clin. Med. 62, 724 (1963), it was observed that the compound I decreases by 20% the platelet stickiness, 4 hours after the administration of 50 mg/kg P.O. of the product in the rabbit.

The inhibiting action of compound I on the aggregation of erythrocytes induced by Dextran was evidenced in vitro on erythrocytes from human, dog and rabbit, according to the method of Von Kaulla K.N., Arz-neimittelForschung, Drug Research 25 (2) 152–155 (1975). It was found that, at 0.001 and 0.002 molar concentrations, the compound I inhibits totally (100%) the aggregation of erythrocytes induced by Dextran.

The inhibiting action of compound I on the retraction of plasmatic clot was evidenced in vitro. At the concentrations ≧ 1,79 mg/ml of plasma, the compound I inhibits totally (100%) the normal retraction of the clot measured for a lapse of 60 minutes.

The action of compound I on fibrinolytic inhibitors was demonstrated as follows:

The main inhibitors of anti-plasminic type, viz. $\alpha_2$-macroglobulins, $\alpha_1$-anti-trypsins and anti-thrombin III were titrated according to the radial immuno-diffusion techniques.

Three concentrations of compound I were incorporated to a pool of standard plasma and incubated for one hour at 37° C. At non-lytic doses by deficiency (suspended standard clots) the compound I gives a decrease of about 10% of $\alpha_2$-macroglobulins level, a decrease of about 20% of $\alpha_1$-anti-trypsins level and a decrease of about 10% of anti-thrombin III level.

At lytic doses, it was observed a decrease of about 20% of $\alpha_2$-macroglobulins level, while $\alpha_1$ anti-trypsins level decreases of 80% and anti-thrombin III level decreases of 50%.

At non-lytic doses by excess (high concentrations of compound I), it was observed an important decrease of fibrinogen level. $\alpha_2$-macroglobulins, $\alpha_1$-anti-trypsins and anti-thrombin III levels are become null.

The above-described pharmacological properties, as well as the low toxicity allow the use of the compound of the formula I and physiologically tolerable salts thereof in therapy especially in the treatment of thromboembolic diseases and arteriosclerosis.

The pharmaceutical compositions of the present invention contain as active ingredient the compound of the formula I or a physiologically tolerable salt thereof, in admixture or conjunction with a pharmaceutically acceptable carrier such for example, as distilled water, glucose, lactose, starch, talc, ethyl cellulose, magnesium stearate or cocoa butter.

The so-obtained pharmaceutical compositions are advantageously in unit dosage form and may contain from 10 to 500 mg, preferably from 10 to 200 mg, of the active ingredient. They may be in form of tablets, dragees, capsules, suppositories or injectable solutions and be administered by oral, rectal or parenteral route. Nevertheless, the preferred route of administration is the intravenous route of an injectable solution at a dose of from 0.5 to 10 mg/kg/hour, preferably from 0.5 to 2 mg/kg/hour, for 3 to 6 hours.

The following Examples illustrate the preparation of the compound of formula I (the melting points being determined in a capillary tube) and the pharmaceutical compositions thereof.

EXAMPLE 1

4-n-pentyl-6-hydroxy salicylic acid

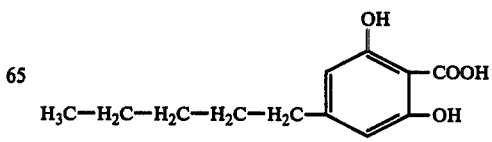

A mixture of 18 g (0.1 mole) of 5-n-pentyl resorcinol and 27.6 g (0.2 mole) of dried potassium carbonate was heated at 175° C. in an autoclave for one hour, under a pressure of carbon dioxide of about 100 atmospheres. After the completion of the carbonation, the reaction mixture was dissolved in 200 ml of tepid water. The so-obtained solution was extracted with 100 ml of ether. The alkaline solution was acidified until pH 1, with an excess of a 4 N solution of hydrochloric acid, then extracted twice with 75 ml of ether. The etheral solution was dried on magnesium sulfate. After evaporation of ether, there were obtained 20 g of a crystalline residue, which recrystallized in 200 ml of cyclohexane, gave 14 g of 4-n-pentyl-6-hydroxy salicylic acid, white crystals melting at 124–125° C.

The starting 5-n-pentyl resorcinol (B.P./0.01 mm Hg = 135–140° C.) was prepared by demethylation of 1,3-dimethoxy-5-n-pentyl benzene by the means of pyridine hydrochloride.

EXAMPLE 2

Formulation for one injectable ampule containing 100 mg of active ingredient

| | |
|---|---|
| 4-n-pentyl-6-hydroxy salicylic acid | 0.100 g |
| glycine | 0.500 g |
| sodium bicarbonate | 0.0374 g |
| for one flask of lyophilizate | |
| water for injectable preparations | 5 ml |

EXAMPLE 3

Formulation for one coated tablet containing 200 mg of active ingredient

| | |
|---|---|
| 4-n-pentyl-6-hydroxy salicylic acid | 0.200 g |
| microcristalline cellulose | 0.098 g |
| dicalcic phosphate | 0.075 g |
| polyvidone carrier | 0.015 g |
| maize starch | 0.095 g |
| magnesium stearate | 0.005 g |
| colloidal silica | 0.002 g |
| carboxymethyl starch | 0.010 g |

-continued

| | |
|---|---|
| Hydroxypropylmethyl cellulose 6 CP | |
| magnesium stearate | |
| glycerin | |
| polyoxyethylene 20 000 | q.s. for coating |
| micronized talc | |
| tartrazine yellow lake | |
| denaturated alcohol | |
| methylene chloride | |

We claim:

1. A pharmaceutical composition useful for thrombolytic therapy containing as active ingredient, in a thrombolytic amount, a α-resorcylic acid derivative of the formula I:

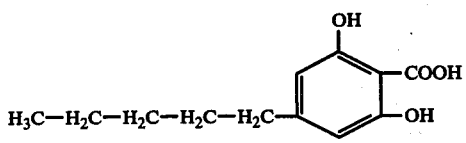

or a physiologically tolerable salt thereof, together with a pharmaceutically acceptable carrier.

2. A pharmaceutical composition as claimed in claim 1 in a dosage form suitable for administration by oral, rectal or parenteral route.

3. A pharmaceutical composition as claimed in claim 1 which contains as active ingredient from 10 to 500 mg of 4-n-pentyl-6-hydroxy salicylic acid or a physiologically tolerable salt thereof.

4. A method for treating thromboembolic diseases, which comprises administering to an animal an effective thrombolytic dose of 4-n-pentyl-6-hydroxy salicylic acid or a physiologically tolerable salt thereof.

5. A method as claimed in claim 4 wherein the compound is administered in unit dosage form containing from 10 to 500 mg of the active ingredient.

6. A method as claimed in claim 4 wherein the active compound is administered by intravenous route at a dose of 0.5 to 10 mg/kg/hour, for 3 to 6 hours.

7. A method as claimed in claim 4, wherein the animal is a human.

* * * * *